(12) United States Patent
Labruzzo

(10) Patent No.: US 10,028,917 B2
(45) Date of Patent: Jul. 24, 2018

(54) BECLOMETHASONE DIPROPIONATE COMPOSITIONS IN MODIFIED-RELEASE GASTRO-RESISTANT MICROSPHERES AND PROCESS FOR OBTAINING THEM

(75) Inventor: Carla Labruzzo, Milan (IT)

(73) Assignee: SOFAR SPA, Trezzano Rosa (MI) (IT)

( * ) Notice: Subject to any disclaimer, the term of this patent is extended or adjusted under 35 U.S.C. 154(b) by 0 days.

(21) Appl. No.: 13/814,642

(22) PCT Filed: Aug. 2, 2011

(86) PCT No.: PCT/IB2011/053430
§ 371 (c)(1),
(2), (4) Date: Feb. 6, 2013

(87) PCT Pub. No.: WO2012/017385
PCT Pub. Date: Feb. 9, 2012

(65) Prior Publication Data
US 2013/0142880 A1 Jun. 6, 2013

(30) Foreign Application Priority Data
Aug. 6, 2010 (IT) .............................. MI2010A1512

(51) Int. Cl.
*A61K 9/50* (2006.01)
*A61K 31/573* (2006.01)
*A61K 9/16* (2006.01)

(52) U.S. Cl.
CPC .......... *A61K 9/5078* (2013.01); *A61K 9/5089* (2013.01); *A61K 31/573* (2013.01); *A61K 9/1676* (2013.01)

(58) Field of Classification Search
CPC .. A61K 9/5078; A61K 31/573; A61K 9/5089; A61K 9/1676
See application file for complete search history.

(56) References Cited

U.S. PATENT DOCUMENTS

| 5,958,458 A | 9/1999 | Norling et al. |
| 2006/0210631 A1 | 9/2006 | Patel et al. |
| 2008/0081070 A1 | 4/2008 | Wilson et al. |

FOREIGN PATENT DOCUMENTS

| EP | 0 375 063 A1 | 6/1990 |
| JP | 07-126153 B2 | 5/1995 |
| WO | 81/02671 A1 | 10/1981 |
| WO | 97/25980 A1 | 7/1997 |
| WO | 01/37808 A1 | 5/2001 |
| WO | 02/074316 A1 | 9/2002 |

OTHER PUBLICATIONS

Steed, K.P., "The In Vivo Behaviour of a Colonic Delivery System: A Pilot Study in Man," International Journal of Pharmaceutics, Elsevier BV, NL, vol. 112, No. 3, Jan. 1, 1994, pp. 199-206, XP002128287.
Saito, M. et al., "New Particle Substance Released in Large Intenstine—Comprises Carrier Coated with Mixt. of Non-Crystal Drug Substance and Macromolecular Substances, Water-Insol. Semipermeable Macromolecular Substance, and Macromolecular Substance," WPI / Thomson, vol. 1995, No. 28, May 16, 1995, XP002630960.
International Search Report dated Feb. 22, 2012, International Application No. PCT/IB2011/053430, International Filing Date: Aug. 2, 2011, Priority Date: Aug. 6, 2012, 9 pages.
Italian Search Report dated Apr. 4, 2011, I0 17099 / IT MI20101512, 8 pages.
Rowe, R.C. et al., "Polymethacrylates," Pharmaceutical Excipients, Fifth Edition, 2006, Pharmaceutical Press, London, pp. 553-560.
European Office Action dated Mar. 18, 2014, Application No. 11 754 741.4-1453, Ref. 11AG16E03, Applicant: Sofar SPA, 6 pages.
EP Search Report dated Jan. 20, 2016, EP Application No. 15195081.3-1453, Sofar S.p.A., 12 pages.
Office Action dated Mar. 3, 2017 issued in European Patent Application No. 15195081.3 (7 pages).

*Primary Examiner* — Adam C Milligan
(74) *Attorney, Agent, or Firm* — Rothwell, Figg, Ernst & Manbeck, P.C.

(57) ABSTRACT

The present invention refers to pharmaceutical beclomethasone dipropionate compositions in modified-release gastro-resistant microspheres and to their oral use in the treatment of inflammatory pathologies of the intestinal tract. Said compositions in microspheres comprise: a) a core consisting of a microsphere of inert material; b) a first intermediate coating comprising beclomethasone dipropionate and at least one physiologically acceptable excipient; c) a second modified-release gastro-resistant coating. The present invention also refers to a process for obtaining said compositions.

29 Claims, 1 Drawing Sheet

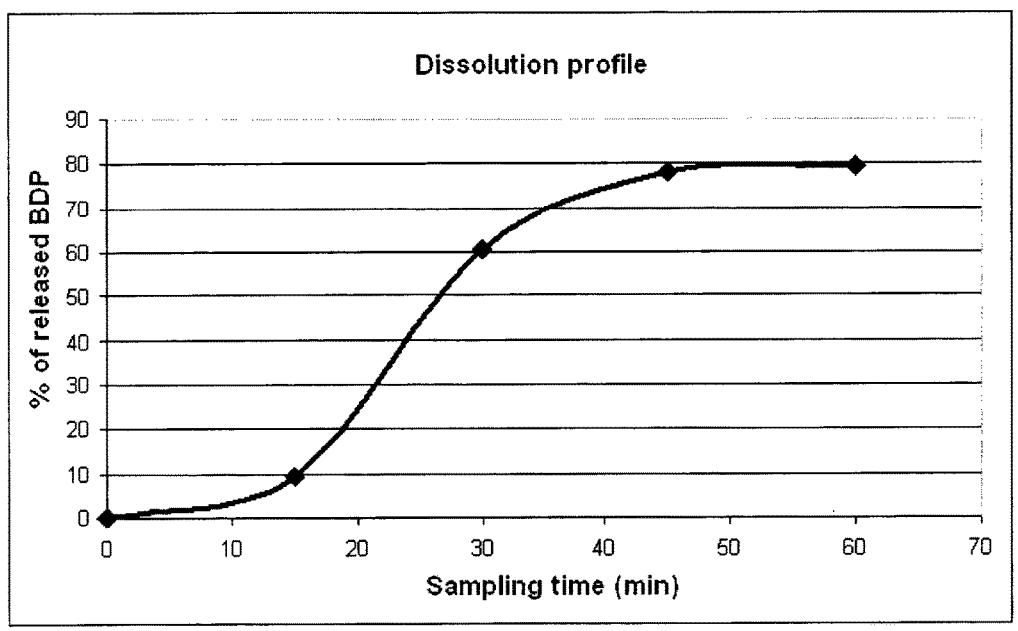

BECLOMETHASONE DIPROPIONATE
COMPOSITIONS IN MODIFIED-RELEASE
GASTRO-RESISTANT MICROSPHERES AND
PROCESS FOR OBTAINING THEM

CROSS-REFERENCE TO RELATED
APPLICATIONS

The present application is a national stage filing under 35 U.S.C. § 371 of PCT/IB2011/053430, filed on 2 Aug. 2011, and claims the benefit of priority to Italian application MI2010A001512 filed 6 Aug. 2010, each application is incorporated herein by reference in its entirety.

BACKGROUND OF THE INVENTION

Chronic intestinal inflammatory diseases are a heterogeneous group of pathologies characterised by alternating phases of activity and remission. These are diseases of an inflammatory nature, with acute or insidious onset, which mainly, but not exclusively affect the intestine, with chronic course and fluctuating activity and progression over time.

These diseases represent an issue of growing importance, also because their incidence and prevalence are increasing either due to the environmental factors typical of industrialised society, or because of the greater diagnostic capability of health professionals.

In this group of diseases, the most significant ones are ulcerative colitis and Crohn's disease, both serious and disabling diseases, which have a negative impact upon the quality of life of patients as well as on their state of health.

Ulcerative colitis is an inflammatory disease of the colon that mainly involves ulceration and bleeding of the intestinal mucosa, severe abdominal pain and diarrhoea. It is a disease that usually has a chronic course, with acute exacerbation in symptoms (abdominal pain, diarrhoea, rectal bleeding, uncontrolled bowel movement, anaemia, weight loss, general poor health). Sometimes it comes with fulminating onset. The incidence of ulcerative colitis fluctuates between 3 and 20 new cases/100000 citizens per year. The most susceptible age group is that between 20 and 40 years old. The complications of the disease include stenosis or intestinal perforation, massive haemorrhage, toxic megacolon, cancer. The complications are responsible for death within a year of the onset of the disease in 4-6% of patients over 60 years old. Crohn's disease is a chronic inflammatory disease that can be located in any part of the orodigestive tract. The age of onset is typically between 15 and 40 years, but it can also occur in infants. In Italy the incidence is 4-5 cases/100000 citizens per year (much higher in Northern Europe and USA), with a prevalence of about 52 cases/100000 citizens. The most frequently affected tract is the terminal ileum and the first tract of the colon. The inflammatory process affects the entire intestinal wall, and it can also cause complications to the adjacent organs. It can be associated with auto-immune phenomena, for example affecting the skin, the eyes and the joints. The most common local complication is represented by intestinal blockage; in various cases, surgical resection of an intestinal tract is necessary. Overall, the disease has a mortality that is roughly double that of the general population.

Corticosteroids or cortisones represent a very important class of drugs used in the therapy of intestinal chronic inflammatory diseases. They are analogous to hormonal substances produced physiologically in the adrenal gland and they are characterised by high anti-inflammation activity.

Glucocorticoids, belonging to the class of corticosteroids, suppress the inflammation through the reduction of the inflammatory exudate, the reduction of the production of inflammatory mediators, the reduction of recruitment of inflammatory cells at the point of inflammation and the reduced activation of inflammatory cells.

Their therapeutic efficacy in inflammatory intestinal diseases has been recognised for about 50 years and, since then, their use has greatly changed the natural history of diseases, which before were diseases dealt with mainly surgically.

Conventional corticosteroids are used exclusively in the moderate-severe forms of disease (for example using high doses of prednisone delivered parenterally).

It is also possible to use cortisones delivered topically, associated with mesalazine enemas, which can for example be particularly effective in the distal forms of ulcerative colitis. However, it should be remembered that the cortisones used systemically, as well as these benefits also involve, particularly if used for repeated cycles, a series of important adverse effects due greatly to their action on the hypophysis-cortico-adrenal system (for example diabetes, osteoporosis, hypertension, cataracts, hirsutism, mental disorders, etc.). Moreover, cortisones administered rectally, whilst having less side effects, do not allow the proximal tracts of the colon to be reached.

Beclomethasone dipropionate (BDP) is a cortisone 500 times more powerful than hydrocortisone, with low water solubility, inactive at the hepatic level, equipped with high receptor affinity, with low intestinal absorption and absence of inhibition of the hypophysis-cortico-adrenal system.

It is currently used in the treatment of ulcerative colitis both delivered orally, in the form of slow-release tablets, and as a liquid enema or rectal foam.

In general, currently, in the treatment of pathologies of the descending colon or of the rectum, there is preferably local application of the active ingredient, through clysters or enemas, to avoid the absorption of the active ingredient during the gastrointestinal journey before it reaches the colon or rectum. Consequently, the release of pharmacologically active agents at the level of the colon or rectum can only be obtained by rectal administration through, for example, foams, liquid enemas, gels or suppositories, associated with a suitable formulation taken orally that, in most cases, experiences better compliance of the patient with respect to rectal administration.

The only pharmaceutical compositions for oral use containing BDP currently on the market (Clipper®) are formulated in slow release tablets.

Patent application US2006/0210631 describes modified-release pharmaceutical compositions for the oral administration of an active ingredient to the colon in which said active ingredient is part of a core.

The fact that the active ingredient is inserted inside a core, like in the formulations of the prior art, can lead to non-homogeneous release thereof and can even not guarantee its complete release.

There is therefore the need for solid oral compositions that ensure higher standards in terms of release, as well as of distribution and homogeneity of content of the active ingredient itself with respect to the compositions of the prior art.

DESCRIPTION OF THE INVENTION

It has been surprisingly found that, precisely through a sophisticated formulation technique, it is possible to obtain improved pharmaceutical compositions containing beclomethasone dipropionate in the form of modified-release gastro-resistant microspheres for oral administration, capable of carrying and releasing at the level of the intestinal mucosa, preferably of the ileum and/or of the colon, a suitable and more modulated amount of active ingredient with respect to what is currently found on the market.

The pharmaceutical composition according to the present invention also ensures a greater contact surface of the active ingredient with the targeted tissue, i.e. the altered mucosa in the intestinal tract, thus allowing a better response to the pharmacological action. The anti-inflammatory effect of beclomethasone dipropionate is indeed in this way amplified by the increased contact surface of the drug with the intestinal mucosa. The pharmaceutical composition according to the present invention differs from what has been described in the prior art since the active ingredient is nebulised on an inert core of microspheres and is not inserted inside said core. Therefore, the pharmaceutical composition according to the present invention leads to a homogeneous and complete release of the active ingredient at the level of the targeted tissue, thus ensuring an improved pharmacological response, as well as having a better distribution and homogeneity of content of the active ingredient.

The pharmaceutical composition according to the present invention also ensures a more site-specific release of active ingredient with respect to what is currently found on the market (for example with respect to Clipper®—slow-release tablets), i.e. it ensures a percentage release of the active ingredient of more than about 70%, preferably equal to about 80%, on the intestinal mucosa, preferably in the ileum, more preferably in the distal ileum, and/or in the colon.

Such a profile of release occurs at pH 7.2 after about one hour from the arrival of the modified-release gastro-resistant microspheres at the aforementioned specific site of release or affected by the pathology (see FIG. 1).

The present invention thus refers to pharmaceutical compositions of beclomethasone dipropionate (henceforth also indicated as "active ingredient" or "BDP") in modified-release gastro-resistant microspheres and to their oral use in the treatment of inflammatory pathologies of the intestinal tract.

Said compositions in microspheres comprise:
a) a core consisting of a microsphere of inert material;
b) a first intermediate coating comprising beclomethasone dipropionate and at least one physiologically acceptable excipient;
c) second modified-release gastro-resistant coating.

The present invention also refers to a process for obtaining said compositions. According to the present invention, the term "microspheres" is meant to include pellets, granules, microgranules with a size preferably smaller than about 2000 microns, even more preferably smaller than about 1000 microns.

According to the present invention, by the term "inert" is meant a substrate, or core, that is pharmacologically inactive and that does not modify the release of the active ingredient from the pharmaceutical form.

According to the present invention, the term "modified-release gastro-resistant microspheres" indicates gastroresistant microspheres containing BDP of the invention that pass unaltered through the gastric tract releasing the active ingredient at the intestinal level, preferably at the level of the ileum, more preferably the distal ileum, and/or of the colon.

According to the present invention, the terms "modified-release gastro-resistant coating" and "modified-release gastro-resistant film" indicate a layer that, when applied on the microspheres coated with BDP according to the present invention, allows said microspheres to pass unaltered through the gastric tract releasing the active ingredient at the intestinal level, preferably at the level of the ileum, more preferably of the distal ileum, and/or of the colon.

The compositions according to the present invention thus comprise a core consisting of a microsphere of an inert material on which beclomethasone dipropionate and at least one physiologically acceptable excipient are applied; the core thus obtained is in turn coated with a modified-release gastro-resistant film, preferably pH-dependent and/or time-dependent.

The microsphere of inert material according to the present invention is characterised by having an average grain size preferably between 100 and 1000 microns, more preferably between 350 and 500 microns.

Said microspheres preferably consist of inert substrates, more preferably diluents. Said diluents according to the invention are preferably selected from microcrystalline cellulose, saccharose, corn starch, lactose and/or a mixture thereof.

The first intermediate coating comprises beclomethasone dipropionate and at least one physiologically acceptable excipient, preferably capable of providing the desired release performance.

Examples of physiologically acceptable excipients are preferably selected from suspending agents and/or glidants, filming agents, plasticizing agents and/or a mixture thereof.

Suspending agents and/or glidants according to the present invention are preferably selected from colloidal anhydrous silica, talc and/or a mixture thereof.

Filming agents according to the present invention are preferably selected from alkyl cellulose, hydroxy alkyl cellulose, polyvinylpyrrolidone (PVP), polyvinyl alcohol (PVA) and/or a mixture thereof. Said alkyl cellulose is preferably selected from methyl cellulose, ethyl cellulose and/or a mixture thereof. Said hydroxy alkyl cellulose is preferably selected from hydroxypropyl methylcellulose (HPMC), hydroxy propyl cellulose (HPC) and/or a mixture thereof.

Plasticizing agents according to the present invention are preferably selected from polyalkylene glycols, glycols and/or a mixture thereof. More preferably, said plasticizing agents are selected from polyethylene glycol (PEG) 400, polyethylene glycol (PEG) 6000, propylene glycol, triethyl citrate, triacetin and/or a mixture thereof. The modified-release gastro-resistant coating according to the present invention preferably comprises polymers and/or copolymers of acrylic acid and/or of methacrylic acid, phthalates and/or a mixture thereof.

Examples of polymers and/or copolymers of acrylic acid and/or of methacrylic acid are those commonly available on the market.

Preferably, said polymers and/or copolymers of acrylic acid and/or of methacrylic acid are preferably selected from copolymer of methacrylic acid type B, copolymer of methacrylic acid type C (Eudragit L100-55) and/or a mixture thereof.

Examples of phthalates according to the present invention are preferably phthalate of hydroxypropyl methylcellulose (HPMC), phthalate of cellulose acetate and/or a mixture thereof.

The modified-release gastro-resistant coating according to the invention can also comprise one or more further physiologically acceptable excipients, preferably plasticizing agents, suspending agents and/or glidants, alkaline agents and/or a mixture thereof.

Plasticizing agents according to the invention are preferably selected from polyalkylene glycols, glycols and/or a mixture thereof. More preferably, said plasticizing agents are selected from polyethylene glycol (PEG) 400, polyethylene glycol (PEG) 6000, propylene glycol, triethyl citrate, triacetin and/or a mixture thereof.

Suspending agents and/or glidants according to the invention are preferably selected from colloidal anhydrous silica (Aerosil 200), talc and/or a mixture thereof.

Alkaline agents according to the invention are preferably selected from inorganic salts of alkaline or alkaline earth metals (the anionic portion of which, which must not negatively influence the adhesive properties of the coating, can preferably consist of borates, silicates, carbonates) and/or ammonia.

Beclomethasone dipropionate is present in the compositions of the invention in an amount that varies preferably between 0.1 and 10% by weight, with respect to the total weight of the composition, more preferably between 0.5 and 5%.

The microspheres of inert material according to the present invention are preferably present in the compositions in an amount that varies between 50 and 70%, with respect to the total weight of the composition, more preferably about 66%.

The modified-release gastro-resistant coating according to the present invention is preferably present in the compositions in an amount that varies between 20 and 40%, with respect to the total weight of the composition, more preferably between 20 and 35%.

The modified-release gastro-resistant microspheres according to the present invention, i.e. the microspheres of inert material on which the beclomethasone dipropionate and the modified-release gastro-resistant coating have been applied, are characterised by an average particle size preferably between 0.200 and 1.60 mm, more preferably between 0.500 and 0.710 mm.

The composition of microspheres according to the invention is then divided into capsules, preferably rigid gelatine capsules, containing an amount of active ingredient per capsule preferably between 0.5 and 10 mg, more preferably between 1 and 5 mg.

A further object of the present invention is a process for preparing said compositions in microspheres that comprises two steps:
I) loading step of the active ingredient (API);
II) step of coating with a modified-release gastro-resistant film.

Said steps mentioned above make it possible to obtain the compositions in microspheres according to the present invention with the desired release performance.

The loading step I) can comprise the following steps:
Ia) pre-heating of the microspheres of inert material in a fluid bed;
Ib) preparation of a suspension containing the active ingredient and at least one physiologically acceptable excipient;
Ic) nebulisation of the aforementioned suspension on the aforementioned microspheres in the fluid bed (spraying step);
Id) drying;
Ie) cooling to a temperature preferably comprised between 25 and 30° C.

Preferably, the suspension according to the aforementioned step Ib) contains beclomethasone dipropionate in association with at least one suspending agent and/or glidant, at least one filming agent, at least one plasticizing agent and at least one hydrophilic solvent, preferably water.

More preferably, the suspension according to the aforementioned step Ib) contains beclomethasone dipropionate in association with at least one suspending agent and/or glidant, at least one filming agent, at least one plasticizing agent and water as the only solvent.

Suspending agents and/or glidants according to the invention are preferably selected from colloidal anhydrous silica (Aerosil 200), talc and/or a mixture thereof.

Filming agents according to the present invention are preferably selected from hydroxyalkyl cellulose, polyvinylpyrrolidone (PVP), polyvinyl alcohol (PVA) and/or a mixture thereof. Said alkyl cellulose is preferably selected from methyl cellulose, ethyl cellulose and/or a mixture thereof. Said hydroxyalkyl cellulose is preferably selected from hydroxypropyl methylcellulose (HPMC), hydroxy propyl cellulose (HPC) and/or a mixture thereof.

Plasticizing agents according to the present invention are preferably selected from polyalkylene glycols, glycols and/or a mixture thereof. More preferably, said plasticizing agents are selected from polyethylene glycol (PEG) 400, polyethylene glycol (PEG) 6000, propylene glycol, triethyl citrate, triacetin and/or a mixture thereof. According to a preferred embodiment of the invention microspheres of microcrystalline cellulose are used with a grain size of between 350 and 500 microns, Aerosil 200 (suspending agent), hydroxypropyl methylcellulose HPMC (filming agent) and purified water (solvent).

In an embodiment of the present invention, the suspension is filtered, preferably with a mesh of between 100 and 300 microns, more preferably with a mesh of between 150 and 180 microns, even more preferably with a mesh of about 150 microns before being nebulised in the fluid bed.

Once the microspheres with the beclomethasone dipropionate applied on their surface have been obtained, the process of the present invention foresees the step of coating the microspheres with a modified-release gastro-resistant film II) that in turn comprises the following steps:

IIa) heating in a fluid bed the microspheres obtained in the loading step (I);

IIb) preparation of a suspension and/or solution containing at least one agent for the modified-release gastro-resistant coating and one or more physiologically acceptable excipients;

IIc) nebulisation of the aforementioned suspension and/or solution on the aforementioned microspheres in the fluid bed (spraying step);

IId) drying;

IIe) cooling to a temperature preferably between 25 and 30° C.

In a preferred embodiment of the present invention the step of modified-release gastro-resistant coating (filming) of the microspheres obtained during the loading step occurs in a single step, so as to ensure the formation of a homogeneous modified-release gastro-resistant film.

In a further embodiment of the present invention the step of modified-release gastro-resistant coating (filming) of the microspheres obtained during the loading step occurs in two steps. It has been observed that the filming in two steps does not affect the dissolution profile of the beclomethasone dipropionate.

Preferably, the suspension and/or solution according to the aforementioned step IIb) contains at least one agent for the modified-release gastro-resistant coating and at least one plasticizing agent, at least one suspending agent and/or glidant, at least one alkaline agent and at least one hydrophilic solvent, preferably water.

The modified-release gastro-resistant coating according to the present invention preferably comprises polymers and/or copolymers of acrylic acid and/or of methacrylic acid, phthalates and/or a mixture thereof.

Examples of polymers and/or copolymers of acrylic acid and/or of methacrylic acid are those commonly available on the market. More preferably, said modified-release gastro-resistant coating comprises the copolymer of methacrylic acid type B, the copolymer of methacrylic acid type C (Eudragit L100-55) and/or a mixture thereof.

Examples of phthalates according to the present invention are preferably phthalate of hydroxypropyl methylcellulose (HPMC), phthalate of cellulose acetate and/or a mixture thereof.

Plasticizing agents according to the invention are preferably selected from polyalkylene glycols, glycols and/or a mixture thereof. More preferably, said plasticizing agents are selected from polyethylene glycol (PEG) 400, polyethylene glycol (PEG) 6000, propylene glycol, triethyl citrate, triacetin and/or a mixture thereof.

Suspending agents and/or glidants according to the invention are preferably selected from colloidal anhydrous silica (Aerosil 200), talc and/or a mixture thereof.

Alkaline agents according to the invention are preferably selected from inorganic salts of alkaline or alkaline earth metals (the anionic portion of which, which must not negatively affect the adhesive properties of the coating, can preferably consist of borates, silicates, carbonates) and/or ammonia.

According to a preferred embodiment of the invention copolymers of methacrylic acid (EUDRAGIT S100) (modified-release gastro-resistant coating), triethyl citrate (plasticizer), colloidal anhydrous silica (Aerosil 200) (suspending agent), a 30% ammonia solution (alkaline agent) and purified water are used.

In a preferred embodiment of the present invention, the suspension for the film of modified-release gastro-resistant coating is filtered with a mesh of between 100 and 300 microns, more preferably with a mesh of between 150 and 180 microns, even more preferably with a mesh of about 180 microns before being nebulised in the fluid bed. The process for the preparation of the pharmaceutical composition according to the present invention is preferably carried out using a single apparatus, more preferably a fluid bed, even more preferably an INNOJET fluid bed of the VENTILUS class.

Moreover, the process for the preparation of the pharmaceutical composition according to the present invention is preferably carried out using at least one hydrophilic solvent, more preferably water as the only solvent.

A further object of the present invention consists of the pharmaceutical compositions that can be obtained according to the process described above.

A further object of the present invention is compositions according to the present invention for use in the treatment of inflammatory pathologies of the intestinal tract.

The aforementioned pathologies are preferably selected from ulcerative colitis and Crohn's disease.

The compositions according to the present invention can be administered to human, meaning both the adult subject and the "paediatric population", where the term "paediatric population" identifies the part of the population from birth up to eighteen years of age.

Moreover, said compositions can be administered to a patient simultaneously, separately or sequentially to conventional therapy.

The following examples illustrate the invention in greater detail without in any way limiting it. The quantitative values expressed in the following examples are expressed in percentage, with respect to the total weight of the composition.

EXAMPLES

Example 1

Onto microspheres of microcrystalline cellulose, a suspension containing BDP, Aerosil 200 (suspending agent), hydroxypropyl methylcellulose HPMC (filming agent) and purified water (solvent) is nebulised.

The amounts by weight of the components of said formulation are summarised in Table 1 below:

TABLE 1

| Component | Dry % | Theoretical amount 100 Kg (Kg) |
|---|---|---|
| BDP | 1.52 | 1.52 |
| HPMC | 2.64 | 2.64 |
| Aerosil 200 | 0.66 | 0.66 |
| Purified water* | — | 43.35 |
| Total weight of the suspension | — | 48.17 |
| Microcrystalline cellulose microspheres | 95.18 | 95.18 |

*Component eliminated during processing

The loading step I) comprises the following steps:
Ia) pre-heating of the microspheres of microcrystalline cellulose in a fluid bed;
Ib) preparation of a suspension containing the active ingredient and at least one physiologically acceptable excipient;
Ic) nebulisation of the aforementioned suspension on the aforementioned microspheres in the fluid bed (spraying step);
Id) drying;
Ie) cooling to a temperature preferably between 25 and 30° C.

The suspension according to step Ib) is prepared according to the following method:
1) dispersing HPMC under agitation in the entire amount of purified water until completely dissolved;
2) adding to phase 1) under stirring: Aerosil 200 and BDP;
3) leaving under stirring for 20-40 minutes;
4) homogenising phase 3) until a homogeneous suspension is obtained.

The loading of the active ingredient onto the microspheres of microcrystalline cellulose is carried out according to the invention using the INNOJET VENTILUS 1 fluid bed. The operating parameters to make the present invention on laboratory scale are summarised in Table 2 given below.

TABLE 2

| Phase | Units | Pre-heating | Spray | Drying |
|---|---|---|---|---|
| Temperature of product | ° C. | 32-36 | 34 | 40 |
| Temperature of air IN | ° C. | 38-40 | 34-36 | 40 |
| Amount of air IN | m³/h | 40-44 | 44-46 | 46-50 |
| Temperature of air OUT | ° C. | 32-36 | 32-36 | 36-40 |
| Nebulisation pressure | bar | | 1.5-1.7 | |
| Peristaltic pump speed | % | | 10-20 | |

TABLE 2-continued

| Phase | Units | Pre-heating | Spray | Drying |
|---|---|---|---|---|
| Flow rate | g/min | | 0.7-2.5 | |
| Duration | | 45-60 min | 4-6 hours | 15 min |

The coating suspension is filtered with a mesh of about 150 microns before being nebulised in the fluid bed.

Example 2

For the preparation of the modified-release gastro-resistant coating, copolymers of methacrylic acid type B (EUDRAGIT S100) (modified-release gastro-resistant coating), triethyl citrate (plasticizer), colloidal anhydrous silica (Aerosil 200) (suspending agent), a 30% ammonia solution (alkaline agent) and purified water are used.

The amounts by weight of the components of said formulation are summarised in Table 3 given below:

TABLE 3

| Component | Dry % | Theoretical amount 100 Kg (Kg) |
|---|---|---|
| EUDRAGIT S100 | 22.03 | 22.03 |
| Triethyl citrate | 11.02 | 11.02 |
| Aerosil 200 | 0.66 | 0.66 |
| 30% ammonia solution | 0.19 | 0.847 |
| Purified water* | — | 135.25 |
| Total weight of the suspension | — | 169.81 |
| coated BPD microspheres 1.52% | 66.10 | 66.10 |

*Component eliminated during processing

In this case the percentage of BDP in the composition in modified-release gastro-resistant microspheres is equal to 1%.

The step of modified-release gastro-resistant coating II) comprises the following sub-steps:

IIa) heating in a fluid bed of the microspheres obtained in the loading step (I);
IIb) preparation of a suspension containing at least one agent for the modified-release gastro-resistant coating and one or more physiologically acceptable excipients;
IIc) nebulisation of the aforementioned suspension on the aforementioned microspheres in the fluid bed (spraying step);
IId) drying;
IIe) cooling to a temperature preferably between 25 and 30° C.

The suspension containing the modified-release gastro-resistant coating is prepared according to the following methods:

1) solubilising under agitation the 30% ammonia solution in about 11% of the total of purified water until completely dissolved;
2) pouring into the final dissolver about 68% of purified water and dispersing under agitation EUDRAGIT S100 for about 15 minutes.
3) combining phase 1) with phase 2) still under agitation, making it percolate far from the mixing rod, avoiding the formation of clots and leaving it under agitation for at least 60 minutes;
4) adding the triethyl citrate and leaving it under agitation for one hour;
5) dispersing, in a separate container, Aerosil 200 in about 20% of purified water and homogenising;
6) combining phase 5) with phase 4) under agitation.

Step II of modified-release gastro-resistant coating is carried out according to the invention using the INNOJET VENTILUS 1 fluid bed.

The operating parameters to make the present invention on a laboratory scale are summarised in Table 4 given below.

TABLE 4

| Phase | Units | Heating | Spray | Drying |
|---|---|---|---|---|
| Temperature of product | ° C. | 29 | 34 | 40 |
| Temperature of air IN | ° C. | 38 | 36-38 | 40 |
| Amount of air IN | m³/h | 40 | 40-44 | 44 |
| Temperature of air OUT | ° C. | 27-29 | 29-34 | 36-40 |
| Nebulisation pressure | bar | | 2 | |
| Peristaltic pump speed | % | | 10-32 | |
| Flow rate | g/min | | 0.7-2.0 | |
| Duration | | 15-30 min | 10-12 ore | 60 min |

The coating suspension is filtered with a mesh of about 180 microns before being nebulised in the fluid bed.

Example 3

According to the method described in Examples 1 and 2 a pharmaceutical composition having the quali-quantitative composition shown below was prepared.

| Component | % by weight | Function |
|---|---|---|
| BDP | 0.50 | API |
| Microcrystalline cellulose | 63.56 | Inert substrate |
| Colloidal anhydrous silica | 1.10 | Suspending agent |
| Hydroxypropyl methylcellulose | 1.74 | Filming agent |
| Copolymers of methacrylic acid | 22.08 | Gastro-resistant agent |
| Triethyl Citrate | 11.02 | Plasticizer |
| Total | 100.00 | |

Example 4

According to the method described in Examples 1 and 2 a pharmaceutical composition having the quali-quantitative composition shown below was prepared.

| Component | % by weight | Function |
|---|---|---|
| BDP | 0.50 | API |
| Microcrystalline cellulose | 63.36 | Inert substrate |
| Colloidal anhydrous silica | 1.10 | Suspending agent |
| Hydroxypropyl methylcellulose | 1.74 | Filming agent |
| Peg 400 | 0.20 | Elasticizer/enhancer |
| Copolymers of methacrylic acid | 22.08 | Gastro-resistant agent |
| Triethyl Citrate | 11.02 | Plasticizer |
| Total | 100.00 | |

Example 5

Dissolution profiles of the modified-release gastro-resistant microspheres containing the active ingredient of 3 batches (Batch 1, Batch 2, Batch 3).

Batch 1

| pH | Time (min) | % release |
|---|---|---|
| 1 | 120 | 0.0 |
| 6.5 | 60 | 0.15 |
| 7.2 | 60 | 81.7 |

Batch 2

| pH | Time (min) | % release |
| --- | --- | --- |
| 1 | 120 | 0.0 |
| 6.5 | 60 | 0.0 |
| 7.2 | 60 | 79.12 |

Batch 3

| pH | Time (min) | % release |
| --- | --- | --- |
| 1 | 120 | 0.0 |
| 6.5 | 60 | 0.0 |
| 7.2 | 60 | 75.93 |

FIG. 1 shows the complete dissolution profile of Batch 2, at pH 7.2.

The invention claimed is:

1. A pharmaceutical composition of modified-release gastro-resistant microspheres, each microsphere consisting essentially of:
   a) a core consisting of a microsphere of inert material;
   b) a first intermediate coating comprising beclomethasone dipropionate, hydroxypropyl methylcellulose (HPMC) as a filming agent in mixture with polyethylene glycol (PEG) 400 as a plasticizing agent, wherein the beclomethasone dipropionate is present in an amount from about 0.1% by weight to about 10% by weight with respect to the total weight of the composition, wherein the HPMC is present in an amount of about 1.74% with respect to the total weight of the composition and wherein the PEG 400 is present in an amount of about 0.2% with respect to the total weight of the composition; and
   c) a second modified-release gastro-resistant coating.

2. A pharmaceutical composition according to claim 1, wherein said microsphere of inert material has an average particle size of between 100 and 1000 microns.

3. A pharmaceutical composition according to claim 2, wherein said inert material is a diluent.

4. A pharmaceutical composition according to claim 3, wherein said diluent is selected from microcrystalline cellulose, saccharose, corn starch, lactose or a mixture thereof.

5. A pharmaceutical composition according to claim 1, wherein said first intermediate coating further comprises at least one physiologically acceptable excipient selected from suspending agents, glidants, or a mixture thereof.

6. A pharmaceutical composition according to claim 5, wherein said suspending agents, glidants or a mixture thereof are selected from colloidal anhydrous silica, talc or a mixture thereof.

7. A pharmaceutical composition according to claim 1, wherein said second modified-release gastro-resistant coating comprises polymers or copolymers of acrylic acid or of methacrylic acid, phthalates or a mixture thereof.

8. A pharmaceutical composition according to claim 7, wherein said polymers or copolymers of acrylic acid or of methacrylic acid are selected from the copolymer of methacrylic acid type B, the copolymer of methacrylic acid type C or a mixture thereof.

9. A pharmaceutical composition according to claim 7, wherein said phthalate is phthalate of hydroxypropyl methylcellulose (HPMC), phthalate of cellulose acetate or a mixture thereof.

10. A pharmaceutical composition according to claim 1, wherein said second modified-release gastro-resistant coating further comprises plasticizing agents, suspending agents or glidants, alkaline agents or a mixture thereof.

11. A pharmaceutical composition according to claim 10, wherein said plasticizing agents of said second modified-release gastro-resistant coating are selected from polyalkylene glycols, glycols or a mixture thereof.

12. A pharmaceutical composition according to claim 10, wherein said suspending agents or glidants of said second modified-release gastro-resistant coating are selected from colloidal anhydrous silica, talc or a mixture thereof.

13. A pharmaceutical composition according to claim 10, wherein said alkaline agents of said second modified-release gastro-resistant coating are selected from inorganic salts of alkaline metals or alkaline earth metals or ammonia or a mixture thereof.

14. A pharmaceutical composition according to claim 1, wherein said microspheres of inert material are present in an amount that varies between 50 and 70%, with respect to the total weight of the composition.

15. A pharmaceutical composition according to claim 1, wherein said second modified-release gastro-resistant coating is present in an amount that varies between 20 and 40%, with respect to the total weight of the composition.

16. A pharmaceutical composition according to claim 1, wherein the modified-release gastro-resistant microspheres have an average particle size of between 0.200 and 1.60 mm.

17. A pharmaceutical composition according to claim 1, wherein it is divided into capsules containing an amount of active ingredient per capsule of between 0.5 and 10 mg.

18. A method for treating inflammatory pathologies of the intestinal tract in a patient in need of such treatment which comprises administering a therapeutically effective amount of the pharmaceutical composition of claim 1 to said patient.

19. A method according to claim 18, wherein inflammatory pathologies of the intestinal tract is ulcerative colitis.

20. A method according to claim 18, wherein inflammatory pathologies of the intestinal tract is Crohn's disease.

21. A pharmaceutical composition according to claim 1, wherein said microsphere of inert material has an average particle size of between 350 and 500 microns.

22. A pharmaceutical composition according to claim 21, wherein said inert material is a diluent.

23. A pharmaceutical composition according to claim 22, wherein said diluent is selected from microcrystalline cellulose, saccharose, corn starch, lactose or a mixture thereof.

24. A pharmaceutical composition according to claim 10, wherein said plasticizing agents are selected from polyethylene glycol (PEG) 400, polyethylene glycol (PEG) 6000, propylene glycol, triethyl citrate, triacetin or a mixture thereof.

25. A pharmaceutical composition according to claim 1, wherein beclomethasone dipropionate is present in an amount that varies between 0.5 and 5% by weight, with respect to the total weight of the composition.

26. A pharmaceutical composition according to claim 1, wherein said microspheres of inert material are present in an amount of about 66%, with respect to the total weight of the composition.

27. A pharmaceutical composition according to claim 1, wherein said second modified-release gastro-resistant coating is present in an amount that varies between 20 and 35%, with respect to the total weight of the composition.

28. A pharmaceutical composition according to claim 1, wherein the modified-release gastro-resistant microspheres have an average particle size of between 0.500 and 0.710 mm.

29. A pharmaceutical composition according to claim 1, wherein the composition is divided into capsules containing an amount of active ingredient per capsule of between 1 and 5 mg.

* * * * *